United States Patent [19]

Allen, Jr.

[11] 4,085,740

[45] Apr. 25, 1978

[54] METHOD FOR MEASURING PHYSIOLOGICAL PARAMETER

[75] Inventor: William P. Allen, Jr., Atlanta, Ga.

[73] Assignee: Lockheed Corporation, Burbank, Calif.

[21] Appl. No.: 538,023

[22] Filed: Mar. 28, 1966

[51] Int. Cl.² .............................................. A61B 5/02
[52] U.S. Cl. ................................. 128/2.05 R; 128/2 S
[58] Field of Search ........................... 343/5 W, 5 PD; 128/2.05, 2.06, 25

[56] References Cited

U.S. PATENT DOCUMENTS

| 2,822,536 | 2/1958 | Sandretto | 343/5 W |
| 2,944,542 | 7/1960 | Barnett et al. | 128/2.05 |
| 3,230,951 | 1/1966 | Teschner | 128/2.05 |
| 3,251,057 | 5/1966 | Buchler et al. | 343/5 W |
| 3,270,339 | 8/1966 | McEuen et al. | 343/5 PD |

Primary Examiner—Verlin R. Pendegrass
Attorney, Agent, or Firm—Billy G. Corber; A. L. Carter

[57] ABSTRACT

A method for measuring such physiological parameters as pulse rate and respiration without physically connecting electrodes or other sensors to the body. A beam of phased energy, for example microwaves, is directed toward the body of a person at a region thereon which undergoes physical displacement corresponding to variations in the parameter being measured. The phase relationship of the energy reflected from the body is compared with that of the transmitted energy to determine the extent of physical movement of the body region as affected by the parameter being measured. The present method may be used as an overt or covert lie detection technique.

10 Claims, 2 Drawing Figures

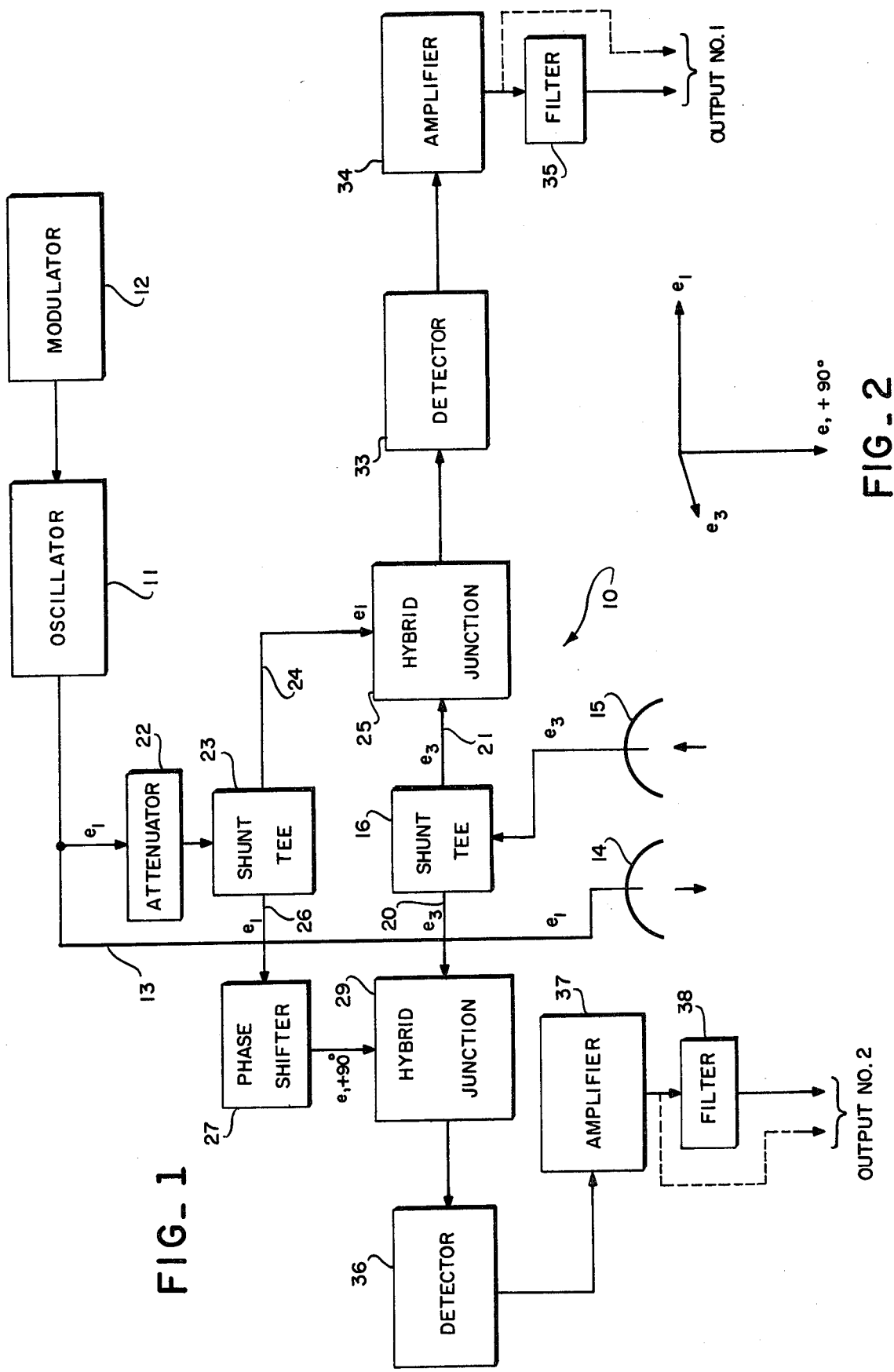

METHOD FOR MEASURING PHYSIOLOGICAL PARAMETER

This invention relates in general to a method of measuring physiological reaction and in particular to a method of measuring physiological reaction without the necessity of encumbering or contacting the body with sensors such as electrodes or the like.

The need often arises for a measuring technique which can enable measurement of various parameters of the human body as evidenced by external movement of portions of the body. By way of example, such parameters as heart beat rate and respiration rate produce small but measurable body movements, and measurement of these movements provides an indication of such factors as the physical condition of the person or his reaction to exertion or applied stress.

While such measurements may be useful for a number of purposes, one purpose for which these measurements have been found to be particularly useful is in the field of lie detection. It has been determined that when a person knowingly makes a false statement, this false statement frequently is accompanied by involuntary and uncontrollable changes in certain body characteristics. Some of these characteristics are respiration rate, pulse rate, and skin resistance. By measuring these characteristics with a machine sometimes known as a polygraph, a skilled operator can determine with a high degree of certainty whether or not the subject undergoing examination is telling the truth.

Lie detection apparatus of the prior art requires that a sensor or sensors be physically attached to or physically associated with the body of the person undergoing examination in order that the characteristic or charcteristics being measured can be sensed. As is known to those skilled in the art, pulse rate and respiration rate each may be measured by means of a sensing device that at least partially encircles a part of the body such as the arm or the chest, respectively. Naturally, the application of such apparatus to a person who may already be nervous undergoing a lie detector examination is likely to make the person even more nervous so that the results of the examination may be adversely affected. Moreover, in situations where it is desirable to subject a person to a lie detector examination covertly so that his physiological reactions will not be influenced by his knowledge of the test being conducted, it obviously is not feasible to use such prior art sensors. Thus, there is need for an apparatus which can function independently of any physical attachment to or physical association with the body and which can measure at least some of the physiological parameters measured by the conventional lie detector and which are indicative of the veracity of the subject.

Accordingly, an object of this invention is to provide an improved technique for measuring physiological body parameters.

Another object of this invention is to provide an improved technique of lie detection.

A further object of this invention is to provide a technique for measuring body parameters without resort to physical attachment to or physical association with the body.

Still another object of this invention is to provide a technique of lie detection wherein no sensors or other apparatus need be attached to or placed in bodily contact with the person being examined.

A still further object of this invention is to provide a technique of lie detection whereby a person may be examined without divulging to such person the fact that he is currently undergoing a lie detector examination.

The exact nature of this invention as well as other objects and advantages thereof will be readily apparent on consideration of the following specification relating to the annexed drawing in which:

FIG. 1 shows in schematic view an embodiment of apparatus which may be used to practice this invention; and FIG. 2 shows a vector diagram depicting certain phase relationships present in the apparatus shown in FIG. 1.

Stated generally, the technique of this invention comprises the use of a remote measuring technique such as radar to detect body movement of a subject corresponding to and caused by such physiological parameters as pulse rate and respiration rate. A beam of radar energy of the appropriate frequency when directed toward the chest, for example, of a subject is capable of producing a return signal which, when appropriately processed, yields a meaningful indication of the pulse rate and respiration rate of the subject and which, therefore, is usable as an indication of the veracity of the subject.

More particularly and with reference to the FIGURE, there is seen a radar transmitting and receiving apparatus indicated generally at 10 and including an oscillator 11 supplied with a modulation signal from modulator 12. Oscillator 11 may, by way of example, be a klystron oscillator of conventional design and having an operating frequency of around 10,000 megacycles. Modulator 12, by way of example, may modulate the output of oscillator 11 at a frequency of 1,000 cps.

The microwave output of oscillator 11 is coupled through line 13, which commonly would be a wave guide of the type known in the prior art, to transmitting antenna 14, which may be of the familiar horn type of antenna. Transmitting antenna 14 is positioned with respect to a person undergoing examination such that this antenna is directed toward the chest of the person being examined or toward another body portion in which movement is produced by the functions of respiration, heart beat, and/or any other body parameter which produces an externally perceptible movement of the body. Reflected r.f. energy from the body of the person undergoing examination is received by receiving antenna 15 and is split by shunt tee 16 into two paths 20 and 21 of equal energy magnitude.

In addition to being supplied to transmitting antenna 14, the r.f. output of oscillator 11 also is supplied through attenuator 22 to shunt tee 23. One output of shunt tee 23 passes through line 24 of hybrid junction 25 where this signal from shunt tee 23 is mixed with that portion of the received signal carried on first path 21. The other output of shunt tee 23 passes through line 26 to a phase shifter 27, whereat the phase of the signal passing through line 26 is shifted by an amount which may be, for example, 90° in either the plus or minus direction. This phase shifted signal then is passed through line 28 to a second hybrid junction 29, whereat the phase shifted signal is mixed with that portion of the received signal passing through second path 20.

Each of the two branches of the receiving circuit is identical following the respective hybrid junctions of these branches. For example, the output signal from hybrid junction 25 passes to detector 33 where this signal is demodulated and then passed on to amplifier 34. The demodulated signal, in the example chosen 1,000 cps, is amplified at 34 and the output of this amplifier may, if desired, form a first output of this apparatus. Alternatively, the amplifier output may be passed through a filter 35 for a purpose described below, whereupon the filter output comprises the first output of the apparatus. Similarly, the output signal from hybrid junction 29 passes through detector 36 and the demodulated signal from this detector passes to amplifier 37. The second output of the apparatus may either be the output of amplifier 37 or it may be this output as passed through filter 38.

In the practice of this invention it should be recalled that the bodily functions of respiration and of heart or pulse cause small but definite movements on at least some portions of the surface of the body. Such movements clearly are evident, for example, in a person who has recently undergone strenuous physical exertion and whose deep breathing resulting from this exertion causes chest movement easily perceptible to the unaided eye. Movements of the chest or other body portions produced through the mental stress resulting from deliberate falsehood, however, may be less perceptible to the human eye, and such movements may consist of a difference in rate as distinguished from a mere difference in amplitude. It is these relatively small and visually imperceptible changes which the technique of this invention is designed to detect.

At a frequency of operation, for example of 9,375 megacycles, the output signal from transmitting antenna 14 produces a wave length in air of 3.2 centimeters. This signal is directed toward a portion of the body, such as the chest cavity, of the subject undergoing examination. The phase of this signal is vectorially represented in FIG. 2, as $e_1$, this being the phase of the signal applied to transmitting antenna 14, to an input of hybrid junction 25, and to the input of phase shifter 27. Of course, the power of the transmitted signal must be sufficiently low to avoid injury to the person at whom it is directed.

Energy transmitted from antenna 14 is reflected from the body portion of the subject and is received at antenna 15. Movement of the chest cavity or other body portion caused either by respiration or heart beat of the subject affects the phase of the received signal relative to transmitted signal phase $e_1$ since such movement changes the length of the path over which the transmitted and received signal travels. This causes rotation of the vector quantity $e_3$ corresponding to the received signal as passed along first path 21 and second path 20. As stated above, the signal represented by vector quantity $e_3$ and passed along first path 21 is combined in hybrid junction 25 with a signal corresponding in phase to the transmitted signal and having a vector phase quantity $e_1$, while the $e_3$ signal passed along line 20 is mixed in hybrid junction 29 with the output signal from phase shifter 27, whose vector relation is $e_1$ plus (or minus) 90°.

When detecting the vector addition of two sinusoids where the phase of one is varied with respect to the other, the signal produced by the detection or demodulation process has an amplitude appearing as a rectified sine wave whose frequency is a function of the relative angular velocity of the two input signal vectors. Thus, the output from detector 33 is a sine wave signal whose frequency depends on the instantaneous relation between vector quantity $e_1$ and $e_3$, while the output from detector 36 is a sine wave signal whose output depends upon the instantaneous vector relation between signals $e_3$ and $e_1$ plus (or minus) 90°. Inasmuch as the relative phase of the received signal $e_3$ is a function of chest cavity movement, in the example taken, of the subject, it is apparent that the output from each of detectors 33 and 36 also is a function of such movement.

Whether or not heart beat, as distinguished from respiration, can be detected by this method appears to be largely dependent on the amount of chest cavity movement produced as a result of heart motion. If heart beat is detected in the signals received by this apparatus, it will be of a different frequency and amplitude from the signal produced by respiration and these two signal components can, if desired, be separated in each of filters 35 and 38 so that either or both of these signal components can be available in both of the outputs of this apparatus. The details of these filters are not shown since it is within the ability of one skilled in the art to design filters having the desired band pass and band rejection characteristics.

With reference again to FIG. 2 of the drawing, it can be seen that for certain positions of the subject with respect to the transmitting and receiving antennas, the received signal $e_3$ may either be very nearly in phase or very nearly 180° out of phase with the transmitted signal $e_1$. Either of these conditions results in a relatively little amplitude change at the output of detector 33, for example, as the result of a given amount of relative phase change in the received signal. For this reason a second channel in the receiver apparatus shown has been provided which mixes the received signal with a signal substantially in quadrature with the transmitted signal. Thus, in a case where the received signal $e_3$ is 180° out of phase with transmitted signal $e_1$, this received signal will be 90° out of phase with the signal $e_1$ plus 90°, so that a given relative phase change in the received signal will produce a maximum amplitude output at output no. 2 while producing only a minimum amplitude output at output no. 1. Thus, the position relative to the transmitting and receiving antennas of the subject undergoing examination need not be rigidly defined for the effective operation of this technique.

Since microwave energy penetrates many substances without an objectionable degree of attenuation, it is possible to conceal the entire apparatus and particularly transmitting antenna 14 and receiving antenna 15 behind a suitable disguising or camouflaging cover so that the person undergoing examination is unaware of the presence of this apparatus and also is unaware that his answers are being subjected to lie detector analysis. For example, antennas 14 and 15 could be concealed behind a panel of a material such as wood or glass fibre, and this panel might comprise a portion of such seemingly conventional office furniture as a desk. Of course, the technique of this invention can be used in an overt manner with the subject undergoing examination being completely aware of the circumstances, with the advantage that no attachment need be made to the subject so as to create fear or apprehension of the impending examination.

The technique set forth herein for lie detection has been found to work quite well in actual experimental practice so long as the subject is reasonably still. Nervous or twitching motion of the subject, if sufficiently pronounced, may cause a signal return that will blank any other lower amplitude signal changes unless the frequency or frequencies of such extraneous and unwanted signal returns can be removed by filtering or other techniques to permit respiration and/or heart beat signals to be present for examination. Of course, such nervous or twitching motion is not limited to the technique disclosed herein, but also adversely affects prior art body movement sensing devices as used with lie detection techniques. The person being interrogated may be clothed in a conventional manner, since body movements normally are transferred to the clothing to an extent sufficient to enable the movement to be sensed by the technique of this invention.

It should be understood of course that the foregoing relates to only a preferred embodiment of the invention and that numerous modifications or alterations may be made therein without departing from the spirit and the scope of the invention as set forth in the appended claims.

What is claimed is:

1. A method of measuring a body function parameter of an organism, comprising the steps of:
   directing a beam of phased energy toward the body of the organism at a region thereon which undergoes physical movement in response to a variation in the body function parameter being measured; and
   receiving phased energy reflected from said region of the body to produce a received signal corresponding to said physical movement of the body region and thus corresponding to said variations in the body function parameter being measured.

2. A method as in claim 1, wherein said step of directing a beam of phased energy includes the step of:
   directing a beam of electromagnetic radiation toward a body at a region thereon which undergoes said physical movement in response to a function of the body, and wherein said step of receiving phased energy as reflected comprises the step of:
   receiving electromagnetic radiation reflected from said region of the body to produce said received signal.

3. A method as in claim 2, wherein said step of analyzing said received signal includes the steps of:
   determining the range of physical body movement which is expected to be caused by a certain body function being measured; and
   filtering said received signal to extract those signal components of said received signal corresponding to said range of expected physical body movement.

4. A method as in claim 2, wherein said step of directing a beam of electromagnetic radiation comprises the step of:
   directing a beam of microwave radar energy toward the body at a region thereof which undergoes said physical movement in response to a function of the body.

5. A method as in claim 4, wherein said step of directing a beam of microwave radar energy comprises the step of:
   directing a beam of microwave radar energy toward the chest region of a human body; and
   filtering the received microwave energy signal reflected from the chest region to select the component of said received signal corresponding to chest region movements resulting from body respiration.

6. A method as in claim 4, wherein said step of receiving reflected electromagnetic radiation comprises the steps of:
   receiving electromagnetic radiation reflected from said region of the body to produce a received signal;
   splitting the received signal into a first received signal portion and a second received signal portion;
   mixing the first received signal portion with microwave energy substantially in phase with the energy in said beam directed toward the body; and
   mixing the second received signal portion with microwave energy substantially out of phase with the energy in said beam directed toward the body.

7. A method of evaluating the response of a person being interrogated, comprising the steps of:
   directing a beam of electromagnetic radiation toward the body of the person at a region thereof which undergoes physical movement in response to a function of the body;
   interrogating the person;
   receiving electromagnetic radiation reflected from said region of the body to produce a received signal corresponding to said physical movement of the body region arising from variations in said body function induced by said interrogation.

8. A method as in claim 7, wherein said step of directing a beam of electromagnetic radiation comprises the step of:
   directing a beam of microwave radar energy toward the body of the person at a region thereof which undergoes physical movement in response to a function of the body; and wherein said step of receiving electromagnetic radiation as reflected comprises the step of:
   receiving microwave radar energy reflected from said region of the body to produce said received signal.

9. A method as in claim 8, wherein said steps of directing a beam of microwave radar energy and receiving reflected microwave radar energy both are performed in a covert manner so that the person being interrogated is not informed that his physical response to such interrogation is being evaluated in this manner.

10. A method as in claim 9, wherein said step of directing a beam of microwave radar energy comprises the step of:
    directing a beam of microwave radar energy toward the chest region of the person.

* * * * *